United States Patent [19] [11] 4,443,216
Chappell [45] Apr. 17, 1984

[54] FLUID PUMP

[75] Inventor: Anthony G. Chappell, Mosman, Australia

[73] Assignee: Wellcome Australia Limited, New South Wales, Australia

[21] Appl. No.: 366,923

[22] Filed: Apr. 9, 1982

[30] Foreign Application Priority Data

Apr. 15, 1981 [AU] Australia ............................. PE8460

[51] Int. Cl.³ .............................................. A61M 5/00
[52] U.S. Cl. .............................. 604/67; 128/DIG. 12; 417/44; 417/412; 604/153
[58] Field of Search ................... 604/67, 34, 118, 121, 604/123, 151–153, 245, 250; 417/44, 326, 412–413, 478

[56] References Cited

U.S. PATENT DOCUMENTS

| 3,620,650 | 11/1971 | Shaw | 604/123 X |
| 3,985,133 | 10/1976 | Jenkins et al. | 604/67 |
| 4,014,318 | 3/1977 | Dockum et al. | 417/412 X |
| 4,277,226 | 7/1981 | Archibald | 604/118 X |

Primary Examiner—Dalton L. Truluck
Attorney, Agent, or Firm—Ladas & Parry

[57] ABSTRACT

A medical infusion pump for use in conjunction with a valved elastomeric pumping chamber. The pump comprises a pair of clamp elements between which the pumping chamber is located and one of the clamp elements is movable relative to the other to effect cyclic compression and expansion of the pumping chamber. The movable clamp element is constituted by an extension of a solenoid armature and such clamp element moves in a direction away from the fixed clamp element, to permit expansion of the pumping chamber, when the solenoid is energized. A compression spring acts against the solenoid armature and serves to bias the movable clamp element in a closing direction when the solenoid is de-energized, whereby a compressive force is applied to the pumping chamber. An electric motor is coupled to the spring by way of a motion translating mechanism and, when energized, the motor functions to change the effective length of the spring and, hence, the biasing force exerted on the movable clamp element.

11 Claims, 12 Drawing Figures

FLUID PUMP

FIELD OF THE INVENTION

This invention relates to a fluid pump device for use in pumping metered quantities of fluid at a predetermined rate. The fluid pump device has particular but non-exclusive application in the injection or extraction of a fluid into or from a person or an animal by way of a hypodermic-type needle and, solely for convenience of reference, the invention is hereinafter described in the context of such application. However, it will be appreciated that the pump device may have other applications, for example, in chemical processes or in food processing where it is required that metered quantities of fluid be transferred between two points.

BACKGROUND OF THE INVENTION

A fluid pump device of the type with which the present invention may be contrasted is disclosed in Australian Patent Application No. 57818/80, filed Apr. 24 1980. Such pump device is intended for use in conjunction with a pumping chamber which is composed of an elastic material and which has a pair of spaced-apart unidirectional valves through which fluid is induced to pass with cyclic compression and expansion of the chamber. The pumping chamber is located between a pair of clamp elements which are moved away from and toward one another with energization and de-energisation respectively of a solenoid to which a moving one of the clamp elements is coupled. Thus, when the solenoid is energised the pumping chamber expands toward its normal full volume, whereby fluid is drawn into the chamber from a fluid source, and when the solenoid is de-energised the pumping chamber is compressed so that it expels the fluid along a delivery line toward a recipient. Compression of the chamber is effected under the influence of a spring which biases the solenoid armature toward an open condition.

When the solenoid is de-energised and the armature is fully open, an electric circuit is closed to establish a time duration T which elapses between de-energisation of the solenoid and the armature reaching a fully open condition. The time duration T may be related either to the instant of de-energisation of the solenoid or, assuming a constant solenoid closing-time period, to the instant of energisation of the solenoid.

Ignoring for the time being various complications that will shortly be discussed, if the time duration T is less than a first predetermined time period $T_1$ then indication is given, for example, that air is present in the fluid delivery line. Conversely, if the time duration T is greater than a second predetermined time period $T_2$ then indication is given, for example, that a blockage is present in the fluid delivery line. Thus, detection is made for compression of the pumping chamber occurring "too quickly" or "too slowly".

However, the time duration T is determined to a large extent by the force exerted by the armature biasing spring and, hence, a high spring force will result in a low duration T and a low spring force will result in a high duration T. Therefore, if the spring force is set sufficiently high, the solenoid armature may be caused to open in time T less than $T_1$ following de-energisation of the solenoid and an erroneous indication may be given that air is in the fluid delivery line. Conversely, if the spring force is sufficiently low, the solenoid armature may be caused to open in time T greater than $T_2$ following de-energisation of the solenoid and an erroneous indication may be given that a blockage exists in the line.

If a simplistic approach were to be taken, the pump device might be constructed so that the spring force is maintained constant and is not adjustably variable. Then, the time duration T would vary solely as a function of the pressure in the fluid delivery line with the spring force being a constant factor.

However, such a simplistic approach is not feasible because the pressure in the delivery line will vary with a pressure differential between the source of the fluid and the fluid delivery point, for example, the injection point in a patient. Thus, different pressure differentials will occur according to the height of the fluid source above or below a patient and in dependence upon whether the fluid is to be injected into a vein or an artery.

Then, assuming that the time periods $T_1$ and $T_2$ are fixed as design parameters of the device, the duration T must be selectively variable to accommodate various possible pressure differentials, and the only way in which the time duration T can be varied independently of hydrostatic conditions is by making the spring force selectively adjustable.

Thus, the terminal end of the time duration T must be placed in a time slot which is relevant to the prevailing pressure differential between the source and delivery points of the pumped fluid AND which is located between the time periods $T_1$ and $T_2$ WHEN normal operating conditions exist. This can be accommodated by providing for manual adjustment of the spring force, as in the case of the device described in the above referenced patent application. However, manual adjustment of the spring force places a heavy onus on the user or operator of the pump device (for example, medical staff in the case of use of the pump device as an infusion pump), and it is desirable that the pump device incorporate a mechanism which is self adjusting as to the location of the time slot in which the time duration T is located according to the pressure differential that exists between the fluid source and the delivery point under normal operating conditions of the device. This is the central issue of the present invention.

SUMMARY OF THE INVENTION

The invention may be defined as providing a fluid pump device for use in conjunction with a chamber having a contained volume which can be reduced elastically and which incorporates or is locatable in circuit with spaced-apart uni-directional valve means through which fluid can be passed with cyclic compression and expansion of the chamber. The pump device comprises:

a pair of spaced-apart clamp elements between which the pumping chamber is located in use of the device, the clamp elements being electrically actuatable to move one relative to the other in an opening direction to permit expansion of the chamber, biasing means for exerting a closing force on the clamp elements following actuation of the clamp elements to an open condition, whereby the chamber is biased to a compressed condition following its expansion, timing means for detecting if the time duration T incurred during compression of the chamber is less than a first predetermined time period $T_1$ or is greater than a second predetermined time period $T_2$, electrically actuatable adjusting means for adjusting the force exerted by the biasing means so that the terminal end of the time duration T is located within a time slot bounded by the predetermined time periods $T_1 < T$ and $T_2 > T$ when the device is subjected to normal operating conditions, and fault indicating means for providing a fault condition indication if, following adjustment of the force exerted by the biasing means, the time duration T is less than the time period $T_1$ or greater than the time period $T_2$ during operation of the device.

Allowance might be made for random excursions of the duration T beyond the period $T_1$ or $T_2$ and a fault condition indication might be made only if the time duration T is, on average, greater than period $T_2$ or less than the period $T_1$ over a predetermined number of cycles of the device. As an alternative, a determination may be made as to the rate of any change which occurs in the value of T over a number of cycles of operation of the device, with a fault condition indication being given with occurrence of a rate of change greater than a predetermined rate.

Therefore, the invention may be further defined as providing a pump device which comprises:

a pair of spaced-apart clamp elements between which the pumping chamber is located in use of the device, the clamp elements being electrically actuatable to move one relative to the other in an opening direction to permit expansion of the chamber, biasing means for exerting a closing force on the clamp elements following actuation of the clamp elements to an open condition, whereby the chamber is biased to a compressed condition following its expansion, timing means for detecting the time duration T incurred during compression of the chamber, electrically actuatable adjusting means for adjusting the force exerted by the biasing means so that the terminal end of the time duration T is located within a time slot bounded by predetermined time periods $T_1 > T$ and $T_2 > T$ when the device is subjected to normal operating conditions, and fault indicating means for providing a fault condition indication if, following adjustment of the force exerted by the biasing means, the time duration T varies at a rate greater than a predetermined rate over successive operating cycles of the pump device.

In one embodiment of the invention the force exerted by the biasing means is adjusted by the electrically actuatable adjusting means so that the time duration T is located within a time slot bounded by the time periods $T_3$ and $T_4$ which satisfy the relationship $$T_1 > T_3 > T_4 > T_2$$

when the pump device is subjected to normal operating conditions.

In operation of the above defined pump device, the chamber is connected by way of a fluid delivery line to a source of fluid to be pumped and the chamber is then operated manually so as to ensure that an unimpeded flow of fluid occurs without any air or other gas bubble being present in the fluid. The fluid delivery line is then coupled to the required delivery point (e.g., a patient who is to receive an infusion of fluid from the source), and the chamber is mounted to the pump device so as to be acted upon by the means which effect cyclic expansion and compression of the chamber. Then, after making a visual inspection for any abnormal conditions, such as an impedance forming kink in the delivery line or inadvertent disconnection of the delivery line from the delivery point, the electrically actuatable means are selectively operated to adjust the force exerted by the biasing means. Thus, having established normal operating conditions for the pump device, the force exerted by the biasing means is automatically adjusted to accommodate the pressure differential that exists between the fluid source and the delivery point for the particular conditions under which the pump device is being used.

Thereafter, the device is actuated so as to perform a normal pumping operation and to detect for any fault conditions.

In use of the pump device as a medical infusion unit, a fault condition will exist in the event of any one of the following happening:

(a) If the fluid delivery line is disconnected from the recipient at the fluid delivery point. Thus time duration T will fall below time period $T_1$.

(b) If any air enters the fluid delivery lines. Under this condition, when the air reaches the chamber the air bubble will compress rapidly with compression of the chamber and the time duration T will fall below that of the time period $T_1$.

(c) If the source is moved in terms of height relative to the recipient of the fluid. Under this condition, which may occur if a support for the source of fluid is "knocked over", the pressure differential between the source and the delivery point will change from that applicable to the initial operating conditions and, depending upon the circumstances, the time duration T may rise above period $T_2$ or fall below the time period $T_1$.

(d) If a blockage occurs in the fluid delivery line, in which case the time duration T will increase beyond the time period $T_2$.

PREFERRED FEATURES OF THE INVENTION

In the pump device as above defined, a first of the clamp elements is preferably fixed and the second of the clamp elements is movable toward and away from the first element to effect compression and expansion of the chamber. Also, the second clamp element is preferably connected to or formed as a portion of the armature of a solenoid which, when energised, causes the second clamp element to move in a direction away from the first clamp element whereby expansion of the chamber is permitted.

Furthermore, the above stated "biasing means" preferably comprises a helical spring device which co-operates with the armature of the solenoid to move the armature to an open condition following de-energisation of the solenoid.

As a further preferred feature of the invention, the above stated "electrically actuatable adjusting means" comprises an electric motor which is coupled to a bearing member for the spring device and which, when energised, functions to change the effective length of and hence the compressive force exerted by the spring device.

The invention will be more fully understood from the following description of a preferred embodiment thereof, the description being given by way of example with reference to the accompanying drawings.

DETAILED DESCRIPTION OF THE INVENTION

Figure 1:
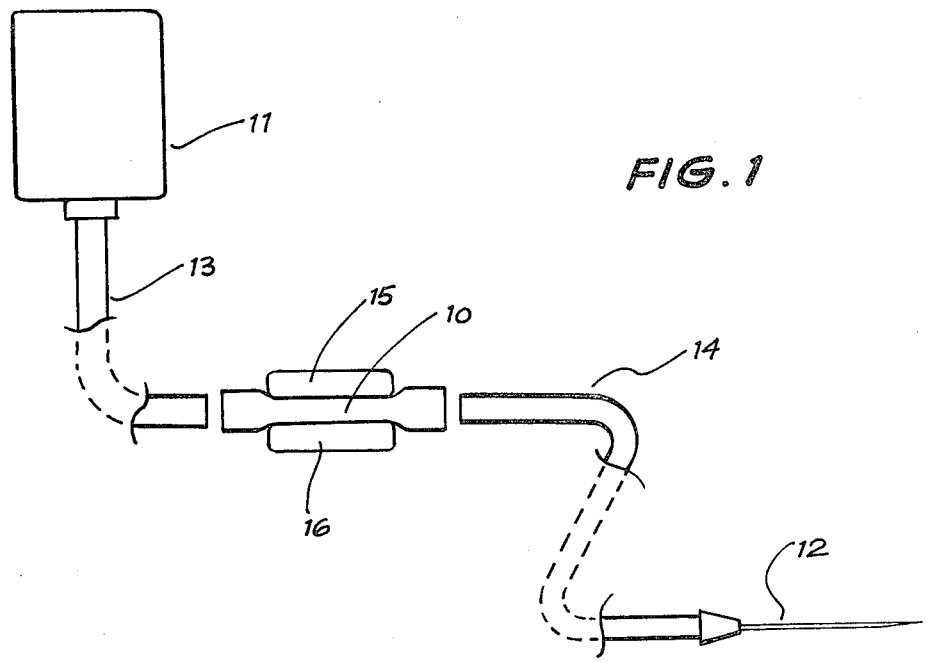
FIG. 1 shows a pumping chamber located in operable relationship with a pair of clamp elements and which is connected by way of a fluid delivery line between a source of injectable fluid and a hypodermic-type needle.
Figure 2:
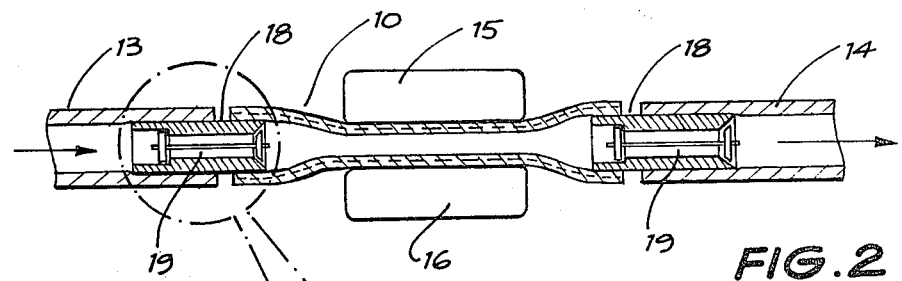
FIG. 2 shows a sectional view of the pumping chamber which is illustrated in FIG. 1.
Figure 3:
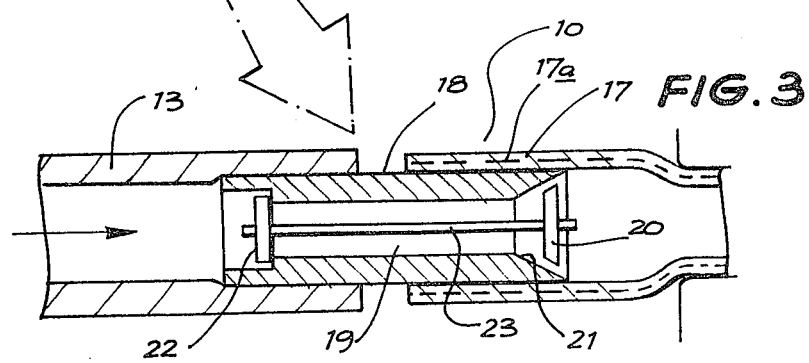
FIG. 3 shows a detailed sectional view of one end portion of the pumping chamber of FIG. 2, with a valve element of the pumping chamber being shown in an open condition.
Figure 4:
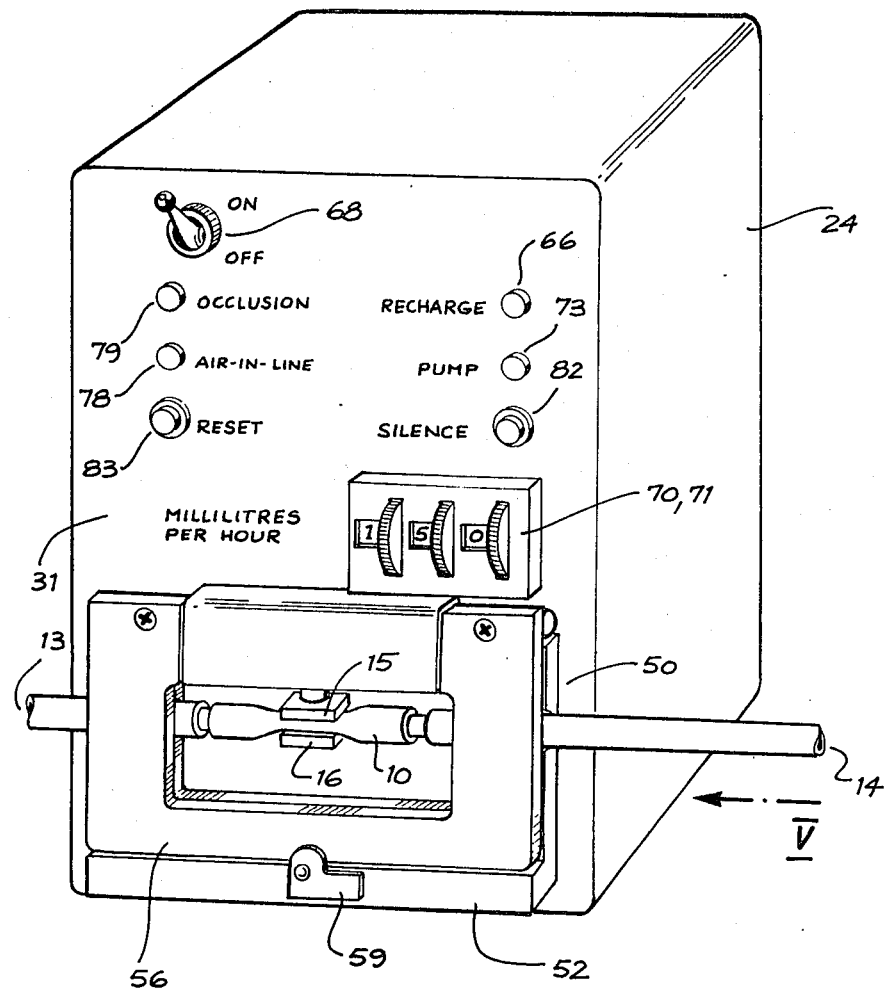
FIG. 4 shows a perspective view of a fluid pump device to which the pumping chamber is mounted.

The pumping chamber 10 as shown in FIGS. 1 to 3 is employed in conjunction with the fluid pump device as shown in FIG. 4 and to which detailed reference will be hereinafter made, and the pumping chamber may be considered as forming a part of a patient circuit. In addition to the pumping chamber 10, the patient circuit comprises a source 11 of injectable fluid, a hypodermic-type needle 12 and two fluid delivery line portions 13 and 14 which respectively connect the pumping chamber 10 to the fluid source 11 and the needle 12.

The pumping chamber 10 is in use located between first and second clamp elements 15 and 16 which form part of the fluid pump device, and the clamp elements are movable toward and away from one another to effect cyclic compression and expansion of the pumping chamber 10. The first clamp element 15 may be regarded as being fixed and the second clamp element 16 is movable in directions toward and away from the first clamp element.

As can best be seen from FIGS. 2 and 3, the pumping chamber 10 comprises a tube 17 which is formed from an elastomeric material (preferably silicone rubber) and which has a yarn or thread reinforcement 17a embedded within its wall. A throat element 18 is located in each end of the tube 17, the throat elements providing for interconnection of the tube 17 with the line portions 13 and 14. A valve member 19 is located in each of the throat elements 18 and, as can best be seen from FIG. 3, each valve member has a head portion 20 which normally closes against a valve seat 21, a T-shaped tail portion 22 through which fluid may pass and a connecting stem 23. The two valve members 19 are formed from a resilient material and they function to permit fluid to pass only in the direction indicated by the arrows shown in FIGS. 2 and 3. Thus, when the clamp element 16 moves away from the clamp element 15, the pumping chamber 10 is expanded to permit fluid flow into the chamber from the source 11, and when the clamp element 16 moves toward the element 15 the pumping chamber is compressed so as to expel the contained fluid in the direction toward the needle 12 from which the fluid is injected into a patient. The spacial relationship of the clamp elements 15 and 16 is adjusted so that even when the elements are separated by a maximum extent, a small degree of clamping is applied to the pumping chamber 10.

The more important components of the fluid pump device to which the pumping chamber 10 is fitted are shown in FIGS. 4 to 9 and are described as follows. Such components are located within or on a casing 24, together with other related components which are not specifically illustrated but which include batteries or a mains-connected power supply, circuit boards for electrical components and hardware items.

The pump device includes a solenoid 25 (FIG. 5) which is located within the casing 24. The solenoid comprises a U-shaped yoke 26, an armature 27 which bridges the pole faces 28 and 29 of the yoke when the solenoid is energised, and a coil 30. The armature 27 incorporates a projection 16 which extends through a cover portion 31 of a casing 24, and the projection 16 does, in fact, constitute the moving clamp element as referred to above. The fixed clamp element 15, which also has been referred to above, is mounted to the cover 31 and the pumping chamber 10 is located between the two clamp elements. When the solenoid is energised, the clamp element 16 moves in a direction away from the fixed clamp element 15 and, when the solenoid is de-energised, the moving clamp moves in a direction toward the fixed clamp element. Thus, de-energisation of the solenoid 25 permits application of a clamping force to the pumping chamber 10 and energisation of the solenoid results in expansion of the pumping chamber.

A helical compression spring 33 is located in one leg 34 of the solenoid yoke and normally projects beyond the pole face 29 of the yoke to contact a mating pole face 35 of the armature. The compression spring 33 acts to bias the armature 27 toward an open condition when the solenoid is de-energised. Although a magnetic attractive force exerted by the solenoid when energised is sufficient to overcome the compressive force of the spring, the spring 33 is operable to effect compression of the pumping chamber 10 following de-energisation of the solenoid coil 30.

The spring 33 is held in place against the armature face 35 and it is held captive within the leg 34 of the solenoid yoke by a bearing member 37. The bearing member 37 is movable in a direction toward and away from the armature 27 by a mechanism which is to be hereinafter described, whereby the biasing force exerted by the spring 33 on the armature can be increased or reduced.

Figure 5:
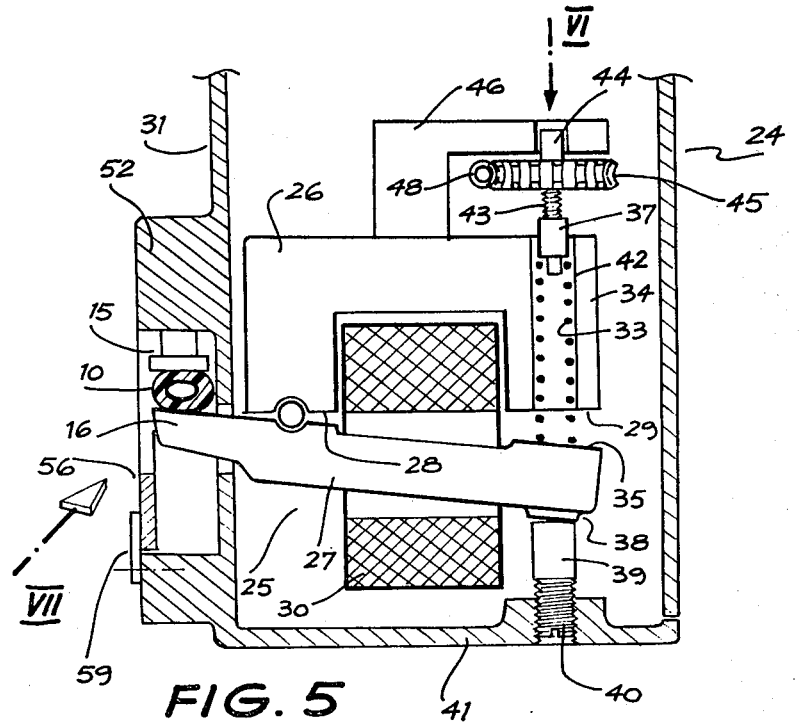
FIG. 5 shows a side elevation view of the interior of the device, as viewed in the direction of Arrow V shown in FIG. 4, and more particularly shows an elevation view of a solenoid device of which one of the clamp elements shown in FIG. 1 forms a part.

The side of the armature 27 which is opposite the pole face 35 is fitted with a contact element 38 (herein referred to as a moving contact element) and the moving contact 38 engages with a fixed contact 39 when the armature is fully open as shown in FIG. 5. The fixed contact 39 is carried by a stud 40 which is screw mounted to a wall portion 41 of the casing 24, and the extent to which the stud is screwed into the casing determines the degree of opening of the armature following de-energisation of the solenoid. The position of the stud 40 is adjustable using an Allen key or the like and adjustment of the effective length of the stud determines the volume of fluid which may be pumped by the pumping chamber 10 with each operating cycle of the solenoid.

The spring bearing member 37 projects into an aperture 42 in the yoke leg 34 to engage the adjacent end of the spring 33, and the bearing member is formed with an outwardly projecting screw-theaded spigot 43. The spigot 43 locates within a screwed bore in the hub 44 of a worm wheel 45 and, thus, when the worm wheel 45 is turned in one direction or the other the spigot 43 advances in a direction into or out from the bore of the hub 45. That is, rotational movement imparted to the worm wheel 45 causes rectilinear translation of the spring bearing member 37 and, in this way, the biasing force exerted by the spring 33 is adjustable.

Figure 6:
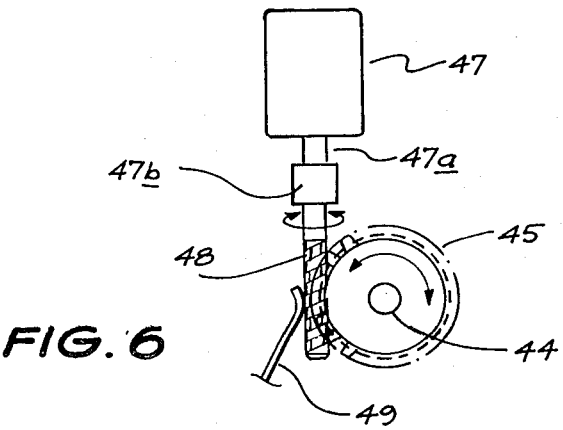
FIG. 6 shows an end elevation view of an actuator which is associated with the solenoid device, the view being taken in the direction of Arrow VI as shown in FIG. 5.

The worm wheel 45 is held in position by a journal arm 46 which is affixed to the solenoid yoke 26, and the arm 46 supports a small d.c. electric motor 47 (FIG. 6). The output shaft 47a of the electric motor is connected by way of a resilient coupling 47b to a worm screw 48 which is held by a leaf spring 49 against the periphery of the gear wheel 45.

When energised, the motor 47 imparts rotary motion to the worm wheel 45 by way of the screw 48, and the worm wheel does in turn impart rectilinear motion to the bearing member 37 as above described.

Figure 7:
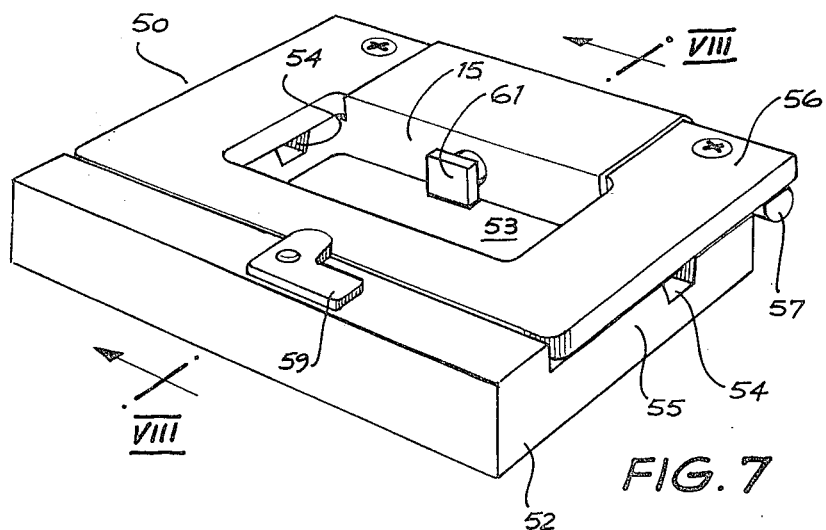
FIG. 7 shows a perspective view of a retaining device which is normally located on or formed as a part of the casing of the pump device (FIG. 4) and which is employed for retaining the pumping chamber in its intended operating position.
Figure 8:
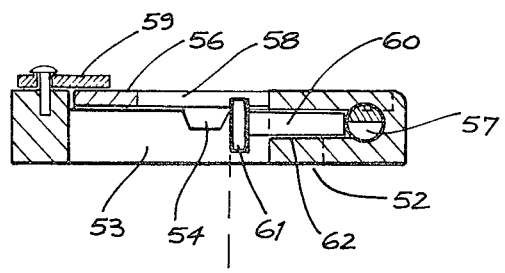
FIGS. 8 and 8A show sectional elevation views of the retaining device, the views being taken in the direction of section plane VIII—VIII as shown in FIG. 7, FIGS. 9 and 9A each show a schematic diagram of an electrical circuit which is embodied in the fluid pump device which incorporates the solenoid device shown in FIG. 4.

During operation of the fluid pump device the pumping chamber 10 and the fluid delivery tubes 13 and 14 are located in position by the retaining device 50 which is mounted to the front face 31 of the casing 24 and which is shown in detail in FIGS. 7 and 8.

The retaining device 50 comprises a first moulding portion 52 which is affixed to or is moulded integrally with the front face 31 of the casing 24. Such moulding portion has a central recess 53 in which the pumping chamber 10 is located and a surrounding wall. A groove 54 is located in opposite edge portions 55 of the surrounding wall for receiving the fluid delivery tubes 13 and 14.

A retaining cover 56 is pivotably mounted to the moulding portion 52 by way of a rotatable hinge pin 57, and the cover serves to hold the delivery tubes 13 and 14 captive in the groove 54. The cover 56 has a central opening 58 which permits viewing of the pumping chamber 10 and it normally is held in a closed position by a latch 59.

Figure 8A:
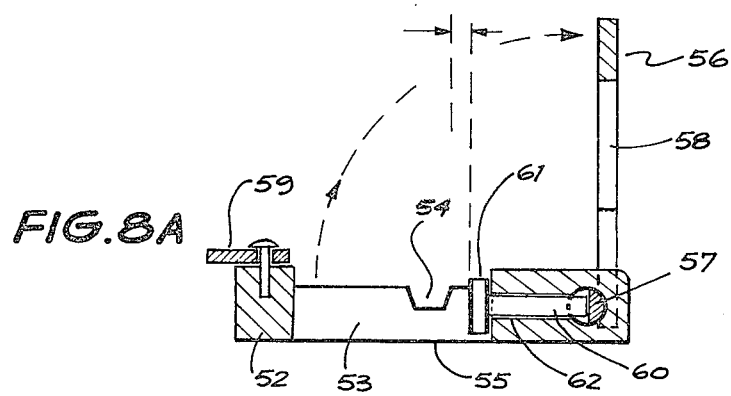

A plunger 15, which includes a stem portion 60 and a head portion 61, is located within a hole 62 in the moulding portion 52 and is moveable between two fixed positions by a cam face on the hinge pin 57. That is, when the cover 56 is opened, as shown in FIG. 8A, the plunger 15 can be moved in a rearward direction to facilitate location of the pumping chamber 10. However, when the cover is closed, the plunger is advanced to the position shown in FIG. 8A and, when in such position, the plunger constitutes the fixed clamp element 15 for the pumping chamber 10.

Further constructional and operational features of the pump device are now described with reference to FIG. 9 of the drawings.

As shown, the pump device comprises a power supply 65 which includes a battery (not shown) and circuitry (including a charge level indicator lamp 66) for testing the state of charge of the battery.

A pulse generator 67 is connected to the power supply by way of a master switch 68 and, in operation of the device, the pulse generator produces a train of square wave pulses. The output from the pulse generator is applied to a divider 69 which is controlled to provide a selected pulse repetition rate output by a manually operable pulse rate selector device 70. The pulse repetition rate might typically be selected to fall within the range of one pulse per minute to 200 pulses per minute and the selected pulse repetition rate is displayed by way of a numeric pulse rate indicator device 71.

The output of the divider 69 is amplified in a first driver 72 and the amplified output is applied to the coil 30 of the solenoid 25. Such output is also applied to an indicator lamp 73 which provides indication of successive energisations of the solenoid.

With application of an energising pulse to the solenoid and resultant closing movement of the armature 27, the following events occur:

(a) The movable clamp element 16 moves in a direction away from the fixed clamp element 15 and the pumping chamber 10 expands.
(b) The spring 33 is compressed.
(c) The normally closed contact elements 38 and 39 open.

Then, when the solenoid 25 is de-energised, the armature 27 will open under the influence of the spring 33, the clamp element 16 will move in a direction toward the fixed clamp element 15, the pumping chamber 10 will be compressed and the contact elements 38 and 39 will close. However, the time duration T which is occupied between de-energisation of the solenoid and closing of the contacts 38 and 39 will be finite and will be determined by at least three factors; namely, the magnitude of the biasing force exerted by the spring 33, the compliance of the material from which the pumping chamber 10 is formed and the pressure differential across the pumping chamber 10.

The output pulses from the driver 72 are applied to first and second timers 74 and 75 and the trailing edge of each output pulse from the driver 72 is employed to initiate the respective timers which then function to provide output pulses having first and second fixed time period $T_1$ and $T_2$ rspectively. The relationships of the solenoid energising pulses, the signal resulting from closure of the contacts 38, 39 and the pulse outputs from the timers 74 and 75 are shown in the timing diagram of FIG. 10. The timing diagram also indicates the time duration T and time periods $T_1$ and $T_2$.

The outputs from the timers 74 and 75 are applied to first and second gates 76 and 77 respectively (the signal applied to gate 77 being inverted), and the signal resulting from closure of the contacts 38, 39 is applied to both of the gates. Thus, with the illustrated circuit configuration, if the contacts 38, 39 close in time duration T less than the time period $T_1$ (which will happen if, for example, air is present in the pumping chamber 10), a logical 1 output will be derived from gate 76. Similarly, if the contacts 38, 39 close in time duration T greater than the time period $T_2$ (which will happen if, for example, a blockage occurs in the pumping chamber fluid circuit), a logical 1 output will be obtained from gate 77.

If an output is derived from either of the gates 76 or 77 and, hence, if a fault condition exists, one or the other of two fault indicating lamps 78 and 79 will be illuminated, an audible alarm 80 will be energised and a disabling circuit 81 will be initiated to apply a disabling signal to the pulse generator 67. Alternatively, if the time duration T falls within the first and second time period $T_1$ and $T_2$ a fault condition will not exist and no output will be produced by the gates 61 and 62.

An alarm silencing switch 82 is provided so that the audible alarm may be silenced if so required.

As above mentioned, the time duration T which is occupied in the closing of the contacts 38, 39 will vary as a function of: the pressure differential across the pumping chamber 10, the compliance of the chamber material and/or the biasing force exerted by the spring 33. Therefore, if a constant biasing force is exerted by the spring 33 and different pressure differentials are encountered in successive applications of the device, it is possible that the time duration T may be less than the fixed time period $T_1$ (if e.g., a low pressure differential is encountered) or greater than the second fixed time period $T_2$ (if e.g., a high differential pressure is encountered). Then, the device may function erroneously to indicate a fault condition.

In order to avoid an erroneous indication of a fault condition and, hence, to accommodate variations in pressure differentials with different applications of the device, the biasing force of the spring is adjusted automatically so that the time duration T always falls within a time slot bounded by time period $T_3$ and $T_4$. The time periods $T_3$ and $T_4$ are fixed to fall between the periods $T_1$ and $T_2$, and the spring biasing force is adjusted by way of the above described motor 47 to create such timing relationship upon commencement of use of the pumping device in a given application and with the existence of normal working conditions of the device in such application. When normal working conditions are perceived to exist (for example, with no blockage or air being perceived to be present in the pumping chamber fluid circuit) a switch 83 is operated to apply energising pulses to the motor 47 by way of a driver 84 and relay contacts which are to be hereinafter described.

Figure 10:
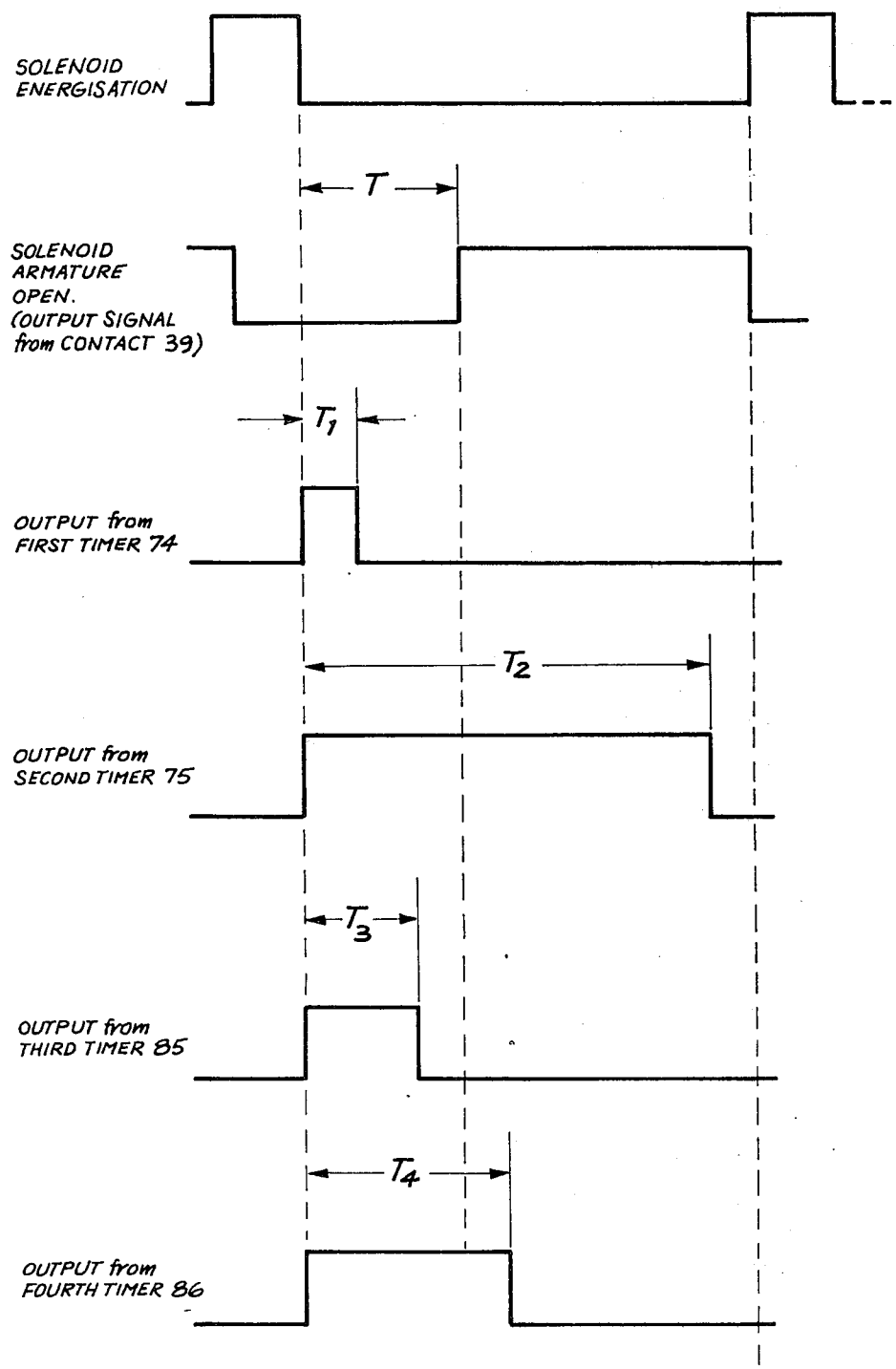
FIG. 10 shows a diagram of timing relationships applicable to the circuit of FIG. 9.

Output pulses from the driver 72 are applied to third and fourth timers 85 and 86 which are initiated to provide output signals for periods $T_3$ and $T_4$ respectively, as shown in FIG. 10. The output signals from the timers 85 and 86 are applied as inputs to gates 87 and 88 respectively (the output from timer 86 being inverted), and the output signal from the contacts 38, 39 is applied to both gates. Thus, if the contacts 38, 39 close in time T less than time period $T_3$, an output will be produced by gate 87, and if the contacts close in time T greater than time period $T_4$ an output will be produced by gate 88. The existence of either of these conditions will require that the biasing force of spring 33 be changed.

The output (if any) from gate 87 is applied to an amplifier 89 which drives a relay 90 and, with energisation of the relay, a moving contact of the relay 90 is switched to terminal a from terminal b whereby pulsed current is caused to pass in a first direction through the electric motor 47 from the motor driving amplifier 84. This results in rotation of the electric motor 47 in a first direction, which causes a reduction in the biasing force exerted by the spring 33.

Similarly, the output (if any) from gate 88 is applied to an amplifier 91 which drives a relay 92. When the relay 92 is energised its moving contact is switched from terminal c to terminal d and pulsed current from the motor driving amplifier 84 passes in a second direction through the electric motor 47, this resulting in the motor being caused to rotate in a second direction so that the biasing force of the spring 33 is increased.

Having automatically adjusted the force of the spring 33 to ensure that the time period T occupied in the closing of contact elements 38, 39 falls within the slot bounded by time period $T_3$ and $T_4$ for a given application of the pump device, the switch 83 is then released so that the motor 47 can no longer be energised. Thereafter, if any air should enter the pumping chamber fluid circuit or if the pressure differential across the pumping chamber 10 should tend towards zero, the time duration T will become less than the period $T_1$ (less than $T_3$) and a low pressure fault indication will be provided by the device. Similarly, if a blockage should occur in the pumping chamber circuit and a high differential pressure across the pumping chamber 10 be experienced, then the time duration T will exceed the time period $T_2$ (greater than $T_4$) and a high pressure fault indication will be provided by the device.

If the duration T is not less than period $T_3$ or not greater than period $T_4$, then no output will be derived from gates 87 or 88 and the indicator lamp 73 which is located in circuit with a NOR gate 93 and an AND gate 94, will be illuminated to signify that no fault condition exists in the fluid circuit.

Figure 9:
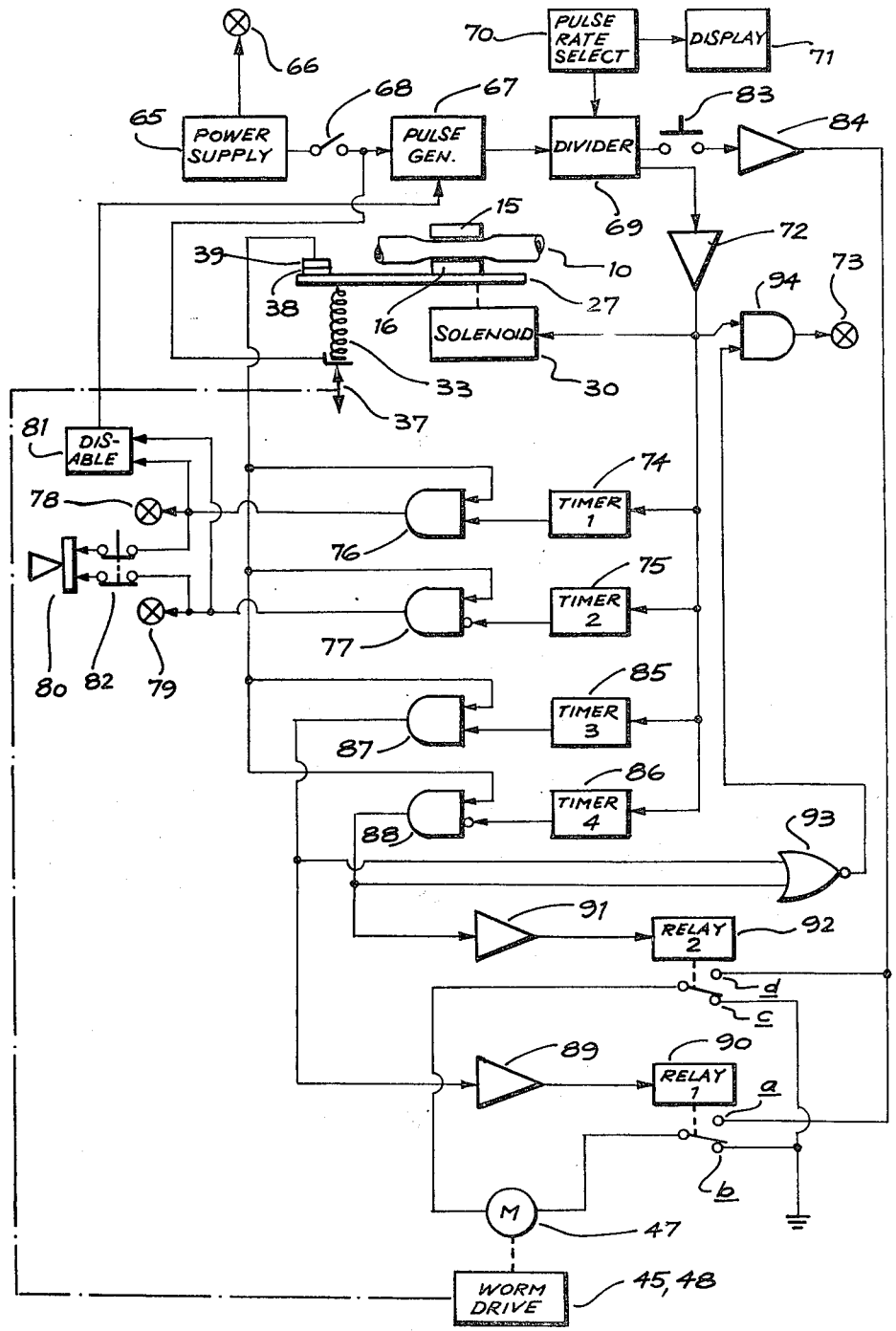
Figure 9A:
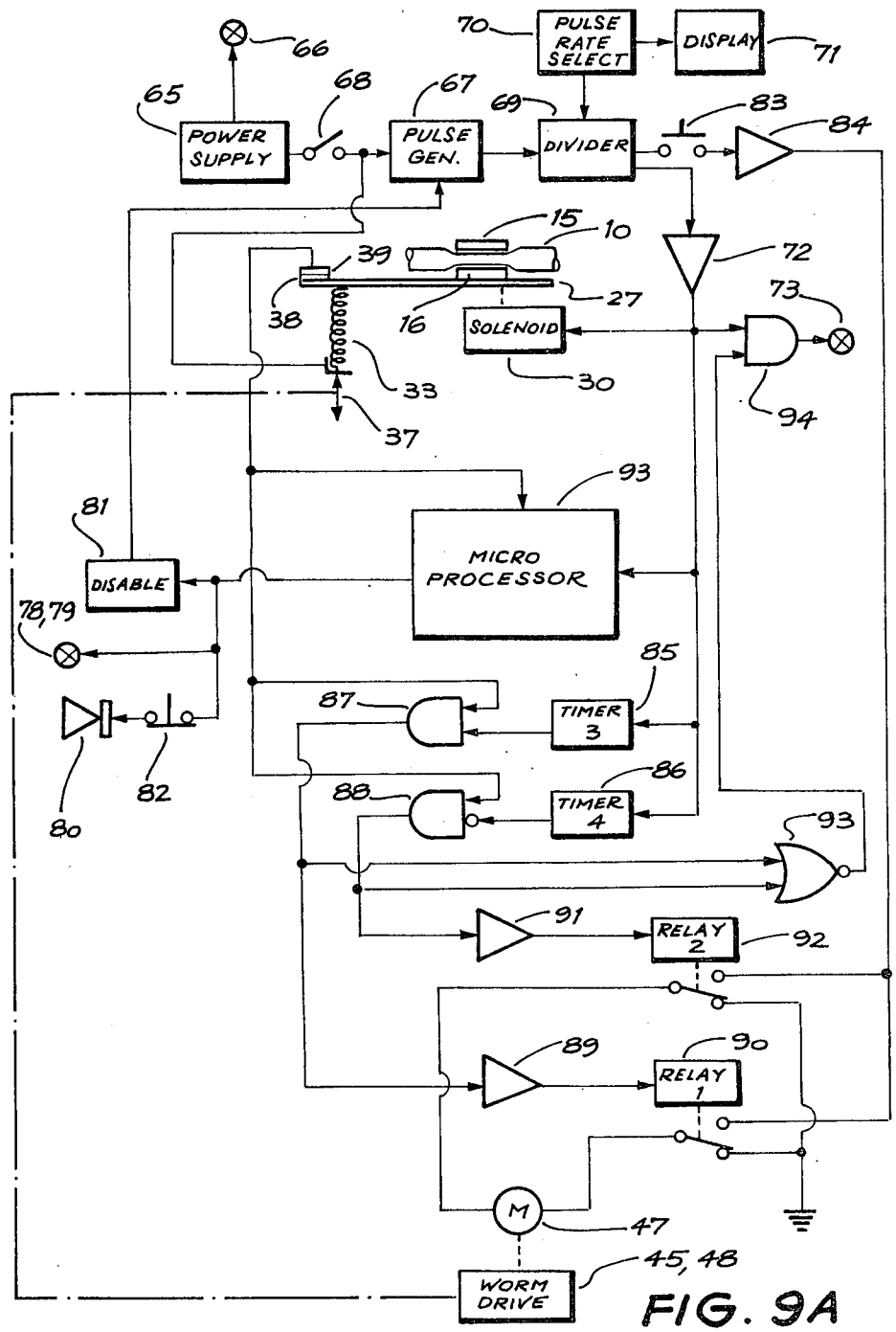

Assuming a maximum pulse repetition rate of the device is 200 pulses per minute and the solenoid energising pulse width is 48 milli-seconds, the above mentioned timing periods may be set as:

$T_1$—45 milli-seconds
$T_2$—245 milli-seconds
$T_3$—85 milli-seconds
$T_4$—95 milli-seconds The circuit which is illustrated in FIG. 9 is largely schematic and various functional requirements of the circuit may be realised in a microprocessor 93 as shown in FIG. 9A. When the microprocessor 93 is employed, allowance may be made for random excursions of the duration T below period $T_1$ or above period $T_2$, and a fault condition indication may be provided if the time duration T is, on average, greater than the period $T_2$ or less than the period $T_1$ over a predetermined number of operating cycles of the device. Alternatively, the microprocessor 93 may be employed to detect for a rate of any change which occurs in the value of T over a number of cycles of operation of the device, and to provide a fault indication if the rate of change is greater than a predetermined (allowable) rate of change.

I claim:

1. A fluid pump device for use in conjunction with a chamber having a contained volume which can be reduced elastically and which incorporates or is locatable in circuit with spaced-apart unidirectional valves through which fluid can be passed with cyclic compression and expansion of the chamber; said pump device comprising:

a pair of spaced-apart clamp elements between which the pumping chamber is located in use of the device, electrically energisable means operable when energized to move one of the clamp elements relative to the other in an opening direction to permit expansion of the chamber, biasing means for exerting a closing force on the clamp elements whereby the chamber is biased to a compressed condition following de-energisation of the electrically energisable means, timing means for detecting the time duration T incurred in compressing the chamber to a predetermined extent against back pressure exerted by fluid within the chamber, fault indicating means for providing a fault condition indication if during operation of the device the time duration T incurred in compressing the chamber is less than a first predetermined time period $T_1$ as a result of an excessively low back pressure being present in the chamber or is greater than second predetermined time period $T_2$ as a result of an excessively high back pressure existing in the chamber, and electrically actuatable adjusting means for adjusting the force exerted by the biasing means so that, when the device is subjected to normal no-fault operating conditions, the terminal end of the time duration T is located within a time slot bounded by the predetermined time periods $T_1 > T$ and $T_2 < T$.

2. A fluid pump device for use in conjunction with a chamber having a contained volume which can be reduced elastically and which incorporates or is locatable in circuit with spaced-apart unidirectional valves through which fluid can be passed with cyclic compression and expansion of the chamber; the pump device comprising:

a pair of spaced-apart clamp elements between which the pumping chamber is located in use of the device;

electrically energizable means operable when energized to move one of the clamp elements relative to the other in an opening direction to permit expansion of the chamber, biasing means for exerting a closing force on the clamp elements whereby the chamber is biased to a compressed condition following de-energization of the electrically energizable means, timing means for detecting the time duration T incurred in compressing the chamber to a predetermined extent against back pressure exerted by fluid within the chamber, fault indicating means for providing a fault condition indication if, during operation of the device, the time duration T incurred in compressing the chamber varies at a rate greater than a predetermined rate over successive operating cycles of the pump device as a result of an excessively low or an excessively high back pressure being present in the chamber, and electrically actuatable adjusting means for adjusting the force exerted by the biasing means so that, when the device is subject to normal, no fault, operating conditions, the terminal end of the time duration T is located within a time slot bounded by first and second predetermined time period $T_1 > T$ and $T_2 < T$ respectively, where the time period $T_1$ is the time within which the chamber will be biased to a compressed condition if an excessively low back pressure exists within the chamber and the time period $T_2$ is the minimum time that will be occupied in biasing the chamber to a compressed condition if an excessively high back pressure exists within the chamber.

3. The fluid pump device as claimed in claim 1 wherein the fault indicating means are arranged to provide a fault condition indication only if the detected time duration T is, on average, greater than the time period $T_2$ or less than the time period $T_1$ over a predetermined number of operation cycles of the pump device.

4. The fluid pump device as claimed in claim 1 or claim 2 wherein the electrically actuatable adjusting means adjust the force exerted by the biasing means so that the terminal end of the time duration T is located within a time slot bounded by predetermined time periods $T_3$ and $T_4$ which satisfy the relationship $T_1 < T_3 < T_4 < T_2$ when the pump device is subjected to normal operating conditions.

5. The pump device as claimed in claim 1 or claim 2 wherein one of the clamp elements is a fixed clamp and the other is a moveable clamp element.

6. The pump device as claimed in claim 5 wherein the electrically energizable means comprises a solenoid device.

7. The pump device as claimed in claim 6 wherein the moveable clamp element is constituted by an extension of an armature portion of the solenoid device, the armature extension being moveable in a direction away from the fixed clamp element when the solenoid is energised.

8. The pump device as claimed in claim 7 wherein the armature portion is pivotably mounted to a fixed yoke portion of the solenoid.

9. The pump device as claimed in claim 7 wherein the biasing means comprises a helical spring which acts against the armature in a direction which induces the armature to move to an open condition following de-energisation of the solenoid.

10. The pump device as claimed in claim 9 wherein the electrically actuated adjusting means comprises an electric motor which is coupled to the spring by way of a motion translating mechanism and which, when energised, imparts translational motion to the spring to thereby change the effective length of the spring and hence the force exerted by the spring on the solenoid armature.

11. The pump device as claimed in claim 10 wherein the electrically actuated adjusting means further comprises third and fourth timing means for detecting whether, during normal operation of the pump device, the terminal end of time duration T falls within a time slot bounded by third and fourth predetermined time periods $T_3$ and $T_4$ which satisfy the relationship $T_1 < T_3 < T_4 < T_2$, and means for energising the electric motor so as to decrease the force exerted by the spring if the time duration T is less than time period $T_3$ or to increase the force exerted by the spring if the time duration T is greater than the time period $T_4$.

* * * * *

UNITED STATES PATENT AND TRADEMARK OFFICE
CERTIFICATE OF CORRECTION

PATENT NO. : 4,443,216

DATED : April 17, 1984

INVENTOR(S) : Anthony G. Chappell

It is certified that error appears in the above-identified patent and that said Letters Patent is hereby corrected as shown below:

Column 3, line 40,

"$T_1>T$" should read "$T_1<T$"

Column 3, line 52

"$T_1>T_3>T_4>T_2$" should read "$T_1<T_3<T_4<T_2$"

Column 11, line 21,

"$T_1>T$ and $T_2<T$" should read "$T_1<T$ and $T_2>T$"

Column 11, line 57, and 58

"$T_1>T$ and $T_2<T$" should read "$T_1<T$ and $T_2>T$"

Signed and Sealed this

Fifteenth Day of July 1986

[SEAL]

Attest:

DONALD J. QUIGG

Attesting Officer

Commissioner of Patents and Trademarks